United States Patent [19]

Tanaka et al.

[11] Patent Number: 4,931,005
[45] Date of Patent: Jun. 5, 1990

[54] APPARATUS FOR THE PRODUCTION OF ELASTIC ABSORBENT

[75] Inventors: Toyoaki Tanaka, Yokohama; Katuzi Ohira, Sagamihara; Akira Nakamura, Chigasaki; Ryosuke Kamei; Akihiro Hashimoto, both of Yokohama, all of Japan

[73] Assignee: Showa Denko Kabushiki Kaisha, Tokyo, Japan

[21] Appl. No.: 304,089

[22] Filed: Jan. 31, 1989

Related U.S. Application Data

[62] Division of Ser. No. 44,373, Apr. 30, 1987, Pat. No. 4,822,668.

[30] Foreign Application Priority Data

| Jul. 18, 1986 | [JP] | Japan | 61-167884 |
| Jul. 31, 1986 | [JP] | Japan | 61-178945 |
| Aug. 13, 1986 | [JP] | Japan | 61-188698 |
| Dec. 11, 1986 | [JP] | Japan | 61-293485 |
| Dec. 22, 1986 | [JP] | Japan | 61-303934 |
| Jan. 5, 1987 | [JP] | Japan | 62-1 |
| Feb. 13, 1987 | [JP] | Japan | 62-29525 |

[51] Int. Cl.$^5$ .............. B28B 5/02; D01G 13/00
[52] U.S. Cl. .................. 425/83.1; 19/145.5; 19/296
[58] Field of Search ............ 425/80.1, 81.1, 82.1, 425/83.1; 19/65 A, 145.5, 296

[56] References Cited

U.S. PATENT DOCUMENTS

| 1,319,486 | 10/1919 | Pirtle | 19/145.5 |
| 3,768,118 | 10/1973 | Ruffo et al. | 19/145.5 |
| 3,772,739 | 11/1973 | Lovgren | 425/81.1 |

FOREIGN PATENT DOCUMENTS

| 204382 | 7/1959 | Fed. Rep. of Germany | 19/296 |
| 3318379 | 11/1984 | Fed. Rep. of Germany | 425/83.1 |
| 3322560 | 1/1985 | Fed. Rep. of Germany | 425/81.1 |
| 62-206025 | 9/1987 | Japan | 19/145.5 |
| 647368 | 2/1979 | U.S.S.R. | 19/296 |
| 916506 | 3/1982 | U.S.S.R. | 425/83.1 |

Primary Examiner—James C. Housel
Assistant Examiner—K. P. Nguyen
Attorney, Agent, or Firm—Sughrue, Mion, Zinn, Macpeak & Seas

[57] ABSTRACT

An apparatus for the preparation of an elastic absorbent composed of a mixed web. Elements of the apparatus can include two supply hoppers for separately supplying pulverized pulp and staple fibers of a synthetic fiber split yarn at a constant mixing ratio with each hopper having a pair of confronting moving belts, two guide mechanisms located below the hoppers, a pair of nip rollers located below the guide mechanisms, a garnet roll located below the pair of nip rollers, a vacuum device located below the garnet roll, and a mesh belt located between the vacuum device and the garnet roll. Each guide mechanism in the apparatus may include at least two gear guides arranged in series. The apparatus operates by feeding the pulverized pulp and the staple fibers of the split yarn from the hoppers to the nip rolls via the guide mechanisms. The nip rolls compress the material, which is then disintegrated and mixed by the garnet roll. The mixture is pulled onto the mesh belt by the vacuum device.

1 Claim, 5 Drawing Sheets

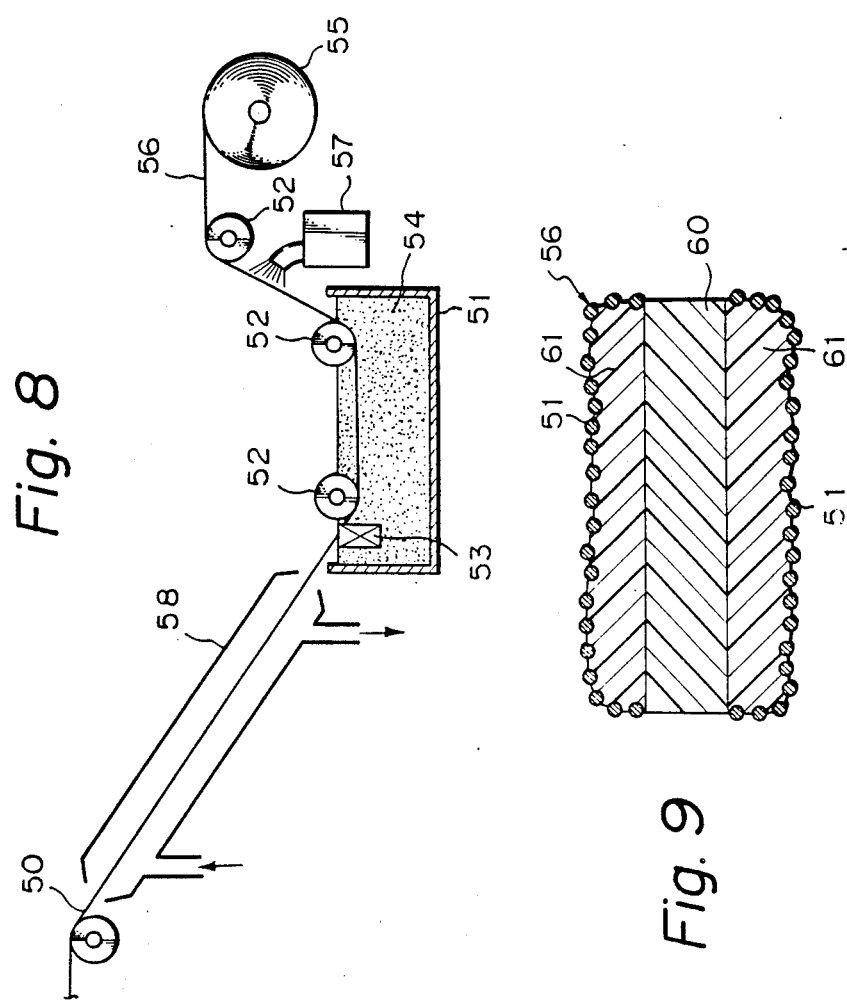

4,931,005

APPARATUS FOR THE PRODUCTION OF ELASTIC ABSORBENT

This is a Division of application Ser. No. 07/044,373, filed on April 30, 1987, now U.S. Pat. No. 4,822,668.

BACKGROUND OF THE INVENTION (1) Field of the Invention

The present invention relates to an elastic absorbent. More particularly, it relates to an elastic absorbent comprising as an absorbing layer a mixed web composed of staple fibers of a split yarn formed of a thermoplastic synthetic material and pulverized cellulose pulp, or an elastic absorbent comprising as an absorbing layer a sandwich structure comprising two sheets of the mixed web and a polymeric water-absorbing agent layer interposed therebetween.

The elastic absorbent of the present invention is useful for the production of sanitary goods such as sanitary napkins and diapers, and packaging trays for fish or meat.

(2) Description of the Related Art

Various absorbents for sanitary goods such as sanitary napkins and paper diapers have heretofore been proposed. In general, the basic structure comprises a liquid permeable surface member, a liquid-impermeable back face member and an absorbing layer interposed therebetween. This absorbing layer is generally composed of a pulp material called "pulverized pulp" or "cotton pulp", and this pulp material is covered with a thin sheet-like member such as tissue paper so that the pulp material is stably wrapped.

Furthermore, an absorbing layer comprising a polymeric water-absorbing agent disposed below a liquid permeable surface member has been proposed.

Sections of typical conventional absorbents are shown in FIGS. 1 and 2. In each of FIGS. 1 and 2, reference numeral 1 represents a liquid-permeable surface member composed of a non-woven fabric or a perforated polyethylene film, and reference numeral 5 represents a liquid-impermeable back face member composed of a synthetic resin film. Reference numeral 2 represents a pulverized cellulose pulp, reference numeral 3 represents a mixture of a pulverized pulp and a polymeric water-absorbing agent, and reference numeral 4 represents a thin sheet-like covering member such as tissue paper.

In the conventional absorbent, a pulp material such as a pulverized pulp and a polymeric water-absorbing agent are used as described above, and since this absorbent has a low strength and a low compression recovery ratio, the absorbent is readily deformed by a kinetic load of a user or a feeling of discomfort is induced. Moreover, the absorbent has problems in that the absorbent is contracted when it absorbs a liquid, and the step of wrapping the pulp material with the thin sheet-like covering member is necessary.

SUMMARY OF THE INVENTION

It is a primary object of the present invention to overcome the above difficulties and provide an elastic absorbent which has a good strength and compression recovery ratio and in which deformation during use or a reduction of comfort when worn is controlled to a minimum level.

Other objects and advantages of the present invention will become apparent from the following description and the accompanying drawings.

In accordance with one aspect of the present invention, there is provided an elastic absorbent, which comprises a substantially homogenous mixture of a pulverized cellulose pulp and staple fibers of a split yarn obtained by splitting a tape-form oriented laminate comprising at least one layer of a synthetic resin having a high melting point and at least one layer of a synthetic resin having a low melting point, in which the layer of the synthetic resin having a low melting point is at least partially exposed to the surface of the oriented laminate, wherein at the crossing points of the staple fibers of the split yarn, the synthetic resin having a low melting point is at least partially fusion-bonded and the staple fibers of the split yarn are connected to one another in the state where the cellulose pulp is partially enclosed therein.

In accordance with another aspect of the present invention, there is provided an elastic absorbent having a sandwich structure comprising upper and lower layers of the above-mentioned mixture of the pulverized cellulose pulp and the staple fibers of the split yarn, and an intermediate layer of a powdery polymeric water-absorbing agent interposed between the two layers.

In accordance with still another aspect of the present invention, there is provided a process for the preparation of an elastic absorbent, which comprises (a) subjecting a split yarn as described above and a sheet-like cellulose pulp simultaneously to an action of one combing roll to cut the split yarn into staple fibers and simultaneously disintegrate the sheet-like cellulose pulp to a pulverized pulp and dry-blending the staple fibers of the split yarn with the pulverized cellulose pulp to obtain a mixed web, or (b) dry-blending a split yarn as described above with pulverized cellulose pulp while cutting the split yarn into staple fibers by a combing roll, to obtain a mixed web, and then heating the mixed web obtained at the step (a) or (b).

In accordance with still another aspect of the present invention, there are provided a process for the preparation of an elastic absorbent, which comprises separately supplying staple fibers of a split yarn as described above and pulverized cellulose pulp to a guide mechanism, compressing both the components integrally, disintegrating the compression product to form a mixed web and then heating the mixed web, and an apparatus for use in carrying out this preparation process, which comprises two supply hoppers for separately supplying a pulverized pulp and staple fibers of a synthetic resin split yarn at a constant mixing ratio, each hopper having a pair of confronting moving belts, two guide mechanisms disposed below said hoppers, a pair of nip rollers disposed below the guide mechanisms, a garnet roll disposed below the pair of the nip rolls, and a vacuum device disposed below the garnet roll with a mesh belt being interposed therebetween.

BRIEF DESCRIPTION OF THE DRAWINGS

FIG. 8 is a diagram schematically illustrating an apparatus for fusion-bonding a polymeric water-absorbing agent powder to a split yarn or a tape-form oriented laminate; and FIG. 9 is an enlarged sectional view illustrating a split yarn to which a polymeric water-absorbing agent powder has been fusion-bonded by the apparatus shown in FIG. 8.

DETAILED DESCRIPTION OF THE PREFERRED EMBODIMENTS

The elastic absorbent of the present invention is composed of staple fibers of a split yarn formed from a thermoplastic resin and a pulverized cellulose pulp.

The split yarn used in the present invention is obtained by splitting a tape-form oriented laminate comprising at least one layer of a synthetic resin having a high melting point and at least one layer of a synthetic resin having a low melting point.

As the tape-form oriented laminate, there is used a tape obtained by drawing a film of a laminate comprising at least one layer of a synthetic resin having a high melting point and at least one layer of a synthetic resin having a low melting point, in which at least one surface is composed of the layer of the synthetic resin having a low melting point, and slitting the drawn film into a tape with a narrow width, or by slitting the film into a tape with a narrow width and drawing the tape. Furthermore, there may be adopted a method in which a laminate tape having a narrow width is directly prepared and the tape is then drawn.

The laminate film can be prepared by various shaping methods such as a calender method, an extrusion method and a casting method. Among them, a co-extrusion method using an inflation die or a T-die is especially preferred.

In preparing a laminate film according to the T-die method or the like, a flat die lip structure may be adopted. A non-flat profile die may also be adopted. The latter die can result in a split yarn having a good feel and a good bulkiness.

Figure 1:
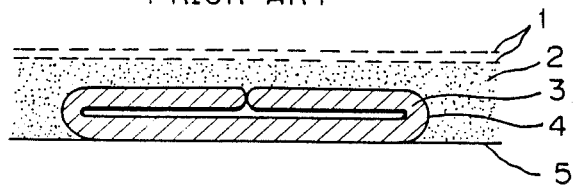
FIGS. 1 and 2 are sectional views of conventional throwaway diapers.
Figure 2:
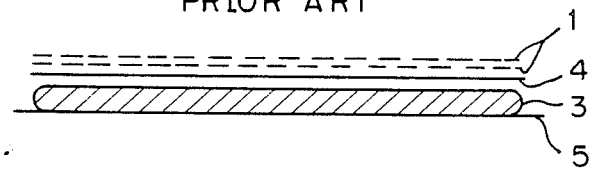
Figure 3:
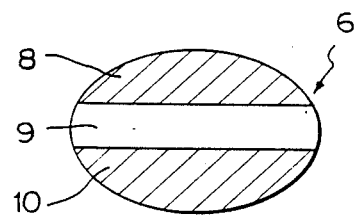
FIG. 3 is a sectional view showing an example of the tape-form oriented laminate used in the present invention.
Figure 4:
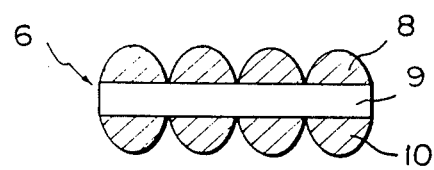
FIG. 4 is a sectional view showing another example of the tape-form oriented laminate used in the present invention.

FIG. 3 is a sectional view illustrating an example of an oriented tape formed from a laminate film obtained by using a flat die, and FIG. 4 is a sectional view of an example of an oriented tape formed from a laminate film obtained by using a non-flat profile die. In FIGS. 3 and 4, reference numeral 6 represents an oriented tape, each of reference numerals 8 and 10 represents a layer of a thermoplastic resin having a low melting point, and reference numeral 9 represents a layer of a thermoplastic resin having a high melting point.

As preferred examples of the laminate film used for the production of the split yarn, there can be mentioned a two-layer laminate of high-melting-point synthetic resin layer/low-melting-point synthetic resin layer (hereinafter referred to as "high/low two-layer laminate"; other laminates are similarly abbreviated), a low/high/low three-layer laminate and a low/high-/low/high/low five-layer laminate.

The number of layers in the tape-form laminate is not particularly critical, but preferably the inner layer is formed of the high-melting-point synthetic resin and the outer layer is formed of the low-melting-point synthetic resin. A larger difference of the melting point is preferred between the high-melting-point synthetic resin and the low-melting-point synthetic resin, and it is generally preferred that the difference in the melting point be 10° C. or more. However, in the case of synthetic resins where the melting point appears sharply, the difference of the melting point may be small.

In general, the high-melting-point synthetic resin is selected from the group consisting of thermoplastic synthetic resins such as crystalline polypropylene, high-density polyethylene, polyesters, nylon 6 and nylon 66.

A low-melting-point thermoplastic synthetic resin having a good bondability to the high-melting-point synthetic resin actually used is used as the low-melting-point synthetic resin. For example, there can be mentioned polyolefins such as low-density polyethylene, linear low-density polyethylene and high-density polyethylene, ethylene/vinyl acetate copolymers, modified polyolefins such as low-density polyethylene, linear low-density polyethylene, high-density polyethylene and polypropylene graft-modified with an unsaturated carboxylic acid or its anhydride such as maleic acid, fumaric acid, itaconic acid, maleic anhydride or itaconic anhydride (graft-modified high-density polyethylene and linear low-density polyethylene are especially preferred and a grafting ratio of 0.3 to 0.36% by weight is preferred), ethylene/acrylate or methacrylate copolymers such as an ethylene/maleic anhydride/methyl methacrylate terpolymer, an ethylene/acrylic acid copolymer and an ethylene/ethyl acrylate copolymer, and thermoplastic resins formed by partially neutralizing an ethylene/methacrylic acid copolymer with a metal such as sodium or zinc (ionomer resins).

As preferred examples of the combination of the high-melting-point and low-melting-point resins, there can be mentioned a combination of crystalline polypropylene and acid-grafted modified linear low-density polyethylene, a combination of crystalline polypropylene and acid-grafted modified high-density polyethylene, a combination of crystalline polypropylene and an ethylene/maleic anhydride/methyl methacrylate terpolymer, ethylene/acrylic acid copolymer or ethylene/ethyl acrylate copolymer, and a combination of crystalline polypropylene and an ionomer resin.

Additives such as a foaming agent, an antioxidant, a lubricant, an ultraviolet absorber, a delusterant, a stabilizer and a flame retardant may be incorporated in the thermoplastic resin according to need.

Any drawing device such as a hot plate, a hot roll or an oven can be used for drawing the laminate film. The drawing temperature and draw ratio are not particularly critical, and optimum conditions are set according to the composition and shape of the laminate film. For example, in the case where a laminate film comprising a polyethylene layer and a crystalline polypropylene layer is slit in the longitudinal direction and is then drawn by a hot roll, preferably the drawing temperature is 100° to 130° C. and the draw ratio is 4 to 10. The thickness of the oriented laminate film or tape is not particularly critical, but preferably is 30 to 100 μm.

The split yarn is formed by splitting the tape-form oriented laminate into a net or complete filaments or fibrils. Splitting is accomplished, for example, according to a method in which the tape-form oriented laminate is contacted with a roll having needles on the surface thereof and rotated in the same direction as the advance direction of the tape. The final fiber diameter is determined according to the lead or pitch of the needles of the splitting roll. Preferably the single fiber fineness (i.e., fibril fineness) of the split yarn is not larger than 100 denier, especially 1 to 40 denier. If the single fiber fineness exceeds 100 denier, the bonding strength of the obtained elastic absorbent is reduced and the compression recovery ratio is as low as about 60%.

A cutter may be used for converting the split yarn to staple fibers, or a combing roll may be used as described hereinafter. In view of the adaptability to mixing with a pulverized cellulose pulp, the adaptability to carding and the feel of fibers, the length of the staple fibers is adjusted to 10 to 100 mm, preferably 10 to 50 mm.

Any cellulose pulp can be used as the pulp in the present invention. For example, there can be used chemical pulp, semi-chemical pulp, chemical ground pulp, and mechanical pulp such as ground pulp. The pulp is pulverized and mixed with the staple fibers of the split yarn. Pulverization of the pulp may be performed simultaneously with cutting of the split yarn into staple fibers, as described hereinafter.

The mixing ratios of the staple fibers of the split yarn and the pulverized cellulose pulp are 10 to 95% by weight and 5 to 95% by weight, respectively, and preferably these mixing ratios is 30 to 95% by weight and 5 to 70% by weight, respectively.

The staple fibers of the split yarn are mixed with the cellulose pulp to form a mixed web. It is generally difficult to mix staple fibers with the pulverized pulp substantially uniformly. Since the length of the pulverized pulp is completely different from that of the staple fiber, falling of the pulverized pulp is readily caused, and the cohesive forces of the pulverized pulp and the staple fibers are very strong. Therefore, in the present invention, the mixing is preferably accomplished according to the following methods.

According to the first mixing method, the split yarn and the sheet-like cellulose pulp are simultaneously subjected to an action of one combing roll, whereby the split yarn is cut into staple fibers and simultaneously, the sheet-like cellulose pulp is disintegrated to a pulverized pulp, and the obtained staple fibers of the split yarn are dry-blended with the pulverized cellulose pulp. This first mixing method will now be described in detail with reference to FIG. 5. A combing roll 11 such as a needle roll or garnet roll is disposed in such a manner that the staple fiber discharge side is exposed to a duct 12. A feed mechanism comprising a transportation stand 14 for a split yarn 13 and a sheet-like pulp 19 and a feed gear 15 is disposed on the open side of the combing roll 11. The lower end of the duct 12 is exposed to an endless mesh belt 16, supported by rolls 20, so that a suction stream generated by a vacuum device 17 arranged on the back side of the belt 16 flows through the duct 12. A feed roll 18 is arranged above the endless mesh belt 16. The inner face of the duct 12 is lined with an electroconductive film so as to prevent electrostatic troubles.

Figure 5:
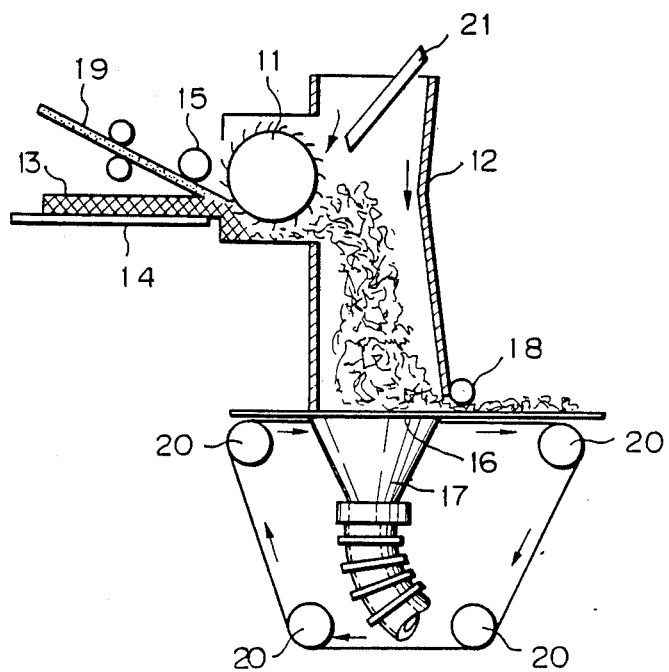
FIGS. 5, 6 and 7 are diagrams schematically illustrating an apparatus for preparing a mixed web of staple fibers of a split yarn and pulverized cellulose pulp.

A regulating plate 21 is inserted into the duct 12 from an upper opening thereof along the air current in the duct 12, and one end of the regulating plate 21 is exposed to the combing roll 11 to form a narrow slit between the end of the regulating plate 21 and the roll 11. The regulating plate 21 has the following function in addition to the function of preventing entanglement in the starting material. Namely, the plate 21 acts as a shelter to the current in the duct 12. Accordingly, on the back of the plate 21, a zone of a swirling turbulent flow as indicated by the arrow in FIG. 5 is formed. The staple fibers of the split yarn discharged in this swirling turbulent flow zone are stirred by the swirling turbulent flow, and thus uniform mixing is attained and the staple fibers are sucked and deposited on the endless mesh belt 16.

In this mixing apparatus, the split yarn 13 and the sheet-like pulp 19 are fed to the gear 15 by the transportation stand 14 and the delivery belt, respectively, and they are quantitatively fed to the combing roll 11 from the gear 15. The combing roll 11 cuts the split yarn 13 into staple fibers and simultaneously disintegrate the sheet-like pulp 19 to pulverized pulp, and the obtained fine staple fibers and pulp are uniformly mixed in the swirling turbulent flow zone and the formed mixed web is sucked and deposited on the endless mesh belt 16.

According to the second mixing method, while the split yarn is being subjected to an action of a combing roll 11 to cut it to staple fibers, the split yarn is dry-blended with pulverized cellulose pulp. This mixing method will now be described with reference to FIG. 6. A combing roll 11 such as a garnet roll having many needles implanted on the peripheral surface thereof is rotated at a high speed, for example, 3,000 to 5,000 rpm, and a split yarn bundle 13 is placed in contact with the combing roll 11 being thus rotated, whereby the split yarn is shaven or cut by the needles.

Figure 6:
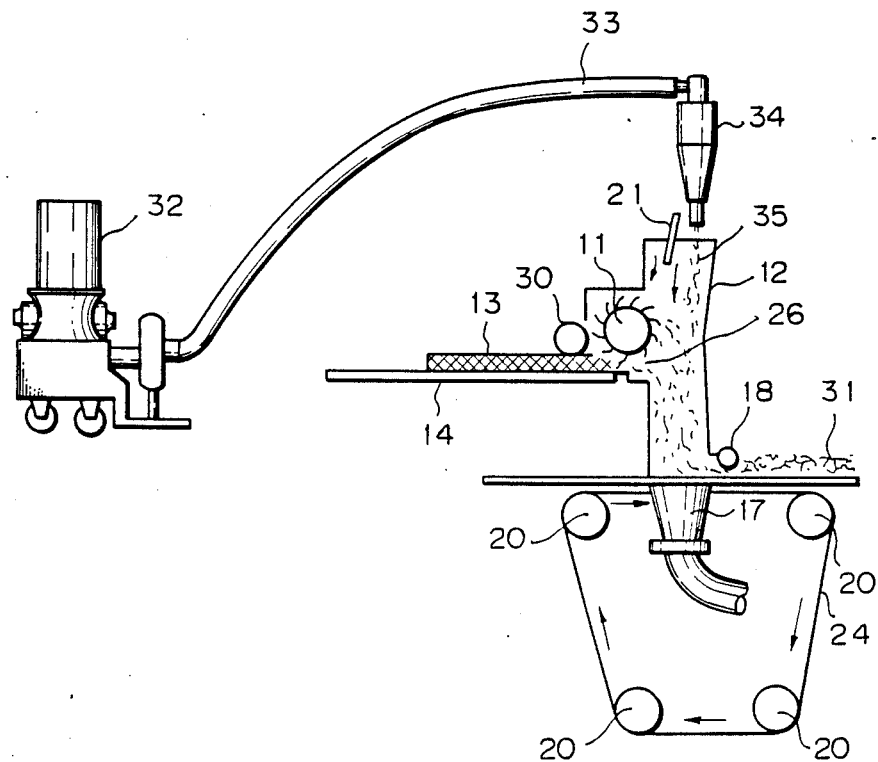

A regulating plate 21 is inserted into a duct 12 from an upper opening thereof along a current in the duct 12, and one end of the regulating plate 21 is exposed to the combing roll 11 to form a narrow slit between the end of the regulating plate 21 and the roll 11. The regulating plate 21 has the following function in addition to the function of preventing entanglement in the starting material. Namely, the regulating plate 21 acts as a shelter to the current in the duct 12. Accordingly, on the back of the plate 21, a zone of a swirling turbulent flow as indicated by the arrow in FIG. 6 is formed. The fine fibers of the split yarn discharged into this swirling turbulent flow zone are stirred and uniform mixing is attained.

A cyclone cylinder 34 is disposed above the duct 12 so that the lower end of the cylinder 34 is exposed to an opening of the duct 12, and the upper portion of the cyclone cylinder 34 is connected to a pulverizer 32 for a pulp, for example, a sheet pulp, through a pipe 33. The pulp pulverized by the pulverizer 32 is passed through a screen mesh (not shown) and fed into the cyclone cylinder 34 through the pipe 33, and the pulverized cellulose is quantitatively dropped into the duct 12 from the lower portion of the cylinder 34.

In the duct 12, fine staple fibers of the split yarn 14 are uniformly mixed with the pulverized pulp 35 and the mixture is sucked and deposited on a screen net 24 through suction by a vacuum device 17 to obtain a mixed web 31.

According to the third mixing method, staple fibers of a split yarn and pulverized cellulose pulp are separately supplied to a guide mechanism, both the components are compressed integrally and the compression product is disintegrated. This mixing method is carried out by using an apparatus comprising two hoppers for separately supplying pulverized cellulose pulp and staple fibers of a split yarn at a constant mixing ratio, each hopper having a pair of confronting moving belts, two guide mechanisms disposed below said hoppers, a pair of nip rolls disposed below the guide mechanisms, a garnet roll disposed below the pair of the nip rolls, and a vacuum device disposed below the garnet roll with a mesh belt being interposed therebetween.

The third mixing method will now be described with reference to FIG. 7. Reference numeral 41 represents a hopper for supplying staple fibers of a split yarn and reference numeral 42 represents a hopper for supplying pulverized pulp, and each hopper has a pair of moving belts 43 on the inner face along the longitudinal direction. The belts 43 are arranged so that the speed can be freely changed. Accordingly, the pulverized pulp and the staple fibers of the split yarn can be quantitatively fed at a constant mixing ratio into the mixing apparatus.

A guide mechanism comprising, for example, three pairs of feed gears 44, is arranged below the hoppers 41 and 42, and the speed of the gears 44 may be the same as the speed of the moving belts 43, or the speed of the gears 44 may be freely changed. The number of the gears 44 is not limited to 6 as shown in FIG. 7, but it is sufficient if the number of the feed gears 44 is at least 2. Note, a belt conveyor can be used instead of the feed gears 44.

Nip rolls 45 and a garnet roll 46 are arranged in sequence below the feed gears 44. The nip rolls 45 are disposed to once grip and compress the material falling in the space, and the garnet roll 46 is disposed to disintegrate and mix the material. A vacuum device 49 is arranged below the garnet roll 46 with a mesh belt 48 being interposed therebetween. The mixture of the staple fibers of the split yarn and the pulverized cellulose pulp is sucked up by the vacuum device 49 to deposit the mixture as a mixed web 47 on the mesh belt 48.

The so-obtained mixed web is then heat-treated, whereby at crossing points of the staple fibers of the split yarn, the low-melting-point synthetic resin is at least partially fusion-bonded and the staple fibers of the split yarn are connected to one another in the state where the pulverized cellulose pulp is partially enclosed therein. The heat treatment is carried out at a temperature higher than the melting point of the low-melting-point synthetic resin but lower than the melting point of the high-melting-point synthetic resin. An appropriate heat treatment temperature depends on the heat treatment method, the heat treatment time and the like. The heat treatment conditions may be determined so that a sufficient dimensional stability is imparted to the elastic absorbent and the softness is not degraded. For example, in the case where a combination of low-density linear polyethylene and crystalline polypropylene are used, preferably the heat treatment is carried out at about 140° C. for 4 to 5 minutes in a hot air-circulating furnace.

By this heat treatment, a sufficient dimensional stability and a sufficient strength (especially in the wet state) are imparted to the elastic absorbent. Accordingly, the step of wrapping the pulverized pulp with a sheet-like material such as tissue paper, which is required in the conventional technique, becomes unnecessary, and the process for the preparation of the absorbent is much simplified. Preferably the basis weight of the obtained elastic absorbent is 100 to 1,000 g/m$^2$.

A powdery polymeric water-absorbing agent may be included into the above-mentioned elastic absorbent comprising the staple fibers of the split yarn and the pulverized cellulose pulp. The water-absorbing power of the elastic absorbent is prominently increased by incorporation of the powdery polymeric water-absorbing agent.

The powdery polymeric water-absorbing agent may be incorporated so that the water-absorbing agent is substantially uniformly distributed in the entire elastic absorbent, or a sandwich structure may be adopted in which an intermediate layer of the powdery polymeric water-absorbing agent is interposed between two mixed webs composed of the staple fibers of the split yarn and the pulverized cellulose pulp. Furthermore, a method may be adopted in which the powdery polymeric water-absorbing agent is substantially uniformly distributed in the mixed web composed of the staple fibers of the split yarn and the pulverized cellulose pulp, and an intermediate layer of the powdery polymeric water-absorbing agent is interposed between two of the so-obtained mixed webs.

A powdery polymeric water-absorbing agent having a water absorption ratio of 10 to 1,000, especially 500 to 1,000 is preferably used. The water absorption ratio referred to herein is determined by immersing the powdery polymeric water-absorbing agent in water to sufficiently swell the water-absorbing agent, removing excessive water by filtration through a screen (80 mesh), measuring the amount (weight) of absorbed water and dividing the amount of absorbed water by the weight of the polymeric water-absorbing agent before swelling with water. As specific examples of the preferred powdery polymeric water-absorbing agent having a water absorption ratio within the above-mentioned range, there can be mentioned sodium polyacrylate, a saponified acrylic acid/vinyl acetate copolymer and a starch/acrylic acid graft copolymer.

The average particle size of the polymeric water-absorbing agent is preferably so small that the low-melting-point synthetic resin layer exposed to the outer surface of the tape-form laminate or the split yarn thereof is covered as densely as possible. In general, the average particle is 10 to 1,000 μm, preferably 10 to 500 μm, especially preferably 10 to 300 μm.

Where the polymeric water-absorbing agent is incorporated, preferably the elastic absorbent comprises 10 to 95% by weight of the staple fibers of the split yarn, 5 to 90% by weight of the pulverized cellulose pulp and up to 40% by weight, especially 10 to 40% by weight, of the polymeric water-absorbing agent. Especially preferably, the elastic absorbent comprises 30 to 75% by weight of the staple fibers of the split yarn, 5 to 50% by weight of the pulverized cellulose pulp and 10 to 30% by weight of the polymeric water-absorbing agent.

The preparation of the mixed web sandwich structure including the intermediate layer of the polymeric water-absorbing agent will now be described. For example, in the above-mentioned method for preparing the mixed web of the staple fibers of the split yarn and the cellulose pulp, the powdery polymeric water-absorbing agent is scattered by a vibrating plate on the mixed web deposited on the endless mesh belt by suction, and the mixed web having the powdery polymeric water-absorbing agent placed thereon is delivered. In another mixing apparatus, a mixed web of the staple fibers of the split yarn and the pulverized cellulose pulp is prepared, and this mixed web is placed on the above-mentioned mixed web having the polymeric water-absorbing agent scattered thereon.

According to a preferred method for distributing the powdery polymeric water-absorbing agent substantially uniformly on the entire mixed web of the staple fibers of the split yarn and the pulverized cellulose pulp, the tape-form laminate or split yarn is heated at a temperature close to the melting point of the low-melting-point resin or higher, the powdery polymeric water-absorbing agent is brought into contact with the heated tape-form laminate or split yarn to fusion-bond the polymeric water-absorbing agent to the outer surface of the exposed low-melting-point synthetic resin layer, and then (after splitting in the case of the tape-form laminate), in the same manner as described above, the split yarn is cut into staple fibers and mixed with the pulverized cellulose pulp. This method will now be described with reference to FIG. 8.

Referring to FIG. 8, a tape-form laminate or split yarn 50 is heated substantially to the melting point of the low-melting-point synthetic resin or higher by a heater 58 in which heated air is circulated. The tape-form laminate or split yarn which has been heated to an extent such that the surface of the low-melting-point synthetic resin layer is substantially fused is fed to a polymeric water-absorbing agent-applying device 51 in which the powdery polymeric water-absorbing agent 54 is contained, and the tape-form laminate or split yarn is passed through the polymeric water-absorbing agent 54 while supported by a roll 52. During this passage, the polymeric water-absorbing agent 54 is fusion-bonded under and appropriate pressing force to the tape-form laminate or split yarn. Preferably the powdery polymeric water-absorbing agent 54 is heated in advance at a temperature at which a degradation of the water-absorbing effect will not occur (for example, 60° to 100° C.).

When the polymeric water-absorbing agent is applied to the split yarn, in order to attain uniform fusion bonding of a large quantity of the polymeric water-absorbing agent and further increase the fusion bonding effect, preferably the split yarn is expanded by an expander 53 and then passed through the polymeric water-absorbing agent 54.

The tape-form laminate or split yarn to which the polymeric water-absorbing agent 54 is fusion-bonded and wound on a bobbin 55. If prior to winding on the bobbin 55, the tape-form laminate or split yarn 56 is passed through an atmosphere humidified by a humidifier 57 and maintained at a relative humidity of 60 to 90%, bonding of the powdery polymeric water-absorbing agent can be further enhanced.

The split yarn obtained according to the abovementioned method has a structure, for example, as shown in FIG. 9. Namely, the split yarn 56 comprises a high-melting-point synthetic resin layer 60 and low-melting-point synthetic resin layers 61, in which the polymeric water-absorbing agent powder 54 is fusion-bonded to the exposed surfaces of the low-melting-point synthetic resin layers.

In the elastic absorbent having a sandwich structure comprising the powdery polymeric water-absorbing agent interposed between two upper and lower mixed webs composed of the staple fibers of the split yarn and the pulverized cellulose pulp, preferably the weight ratio of the staple fibers of the split yarn to the pulp in the upper mixed web is from 40/60 to 95/5, especially from 60/40 to 92/8, particularly especially from 70/30 to 90/10, and in the lower mixed web, the weight ratio of the staple fibers to the pulp is from 5/95 to 40/60, especially from 15/85 to 35/65, particularly preferably from 20/80 to 30/70. If the amount of the pulp is smaller than 5% by weight in the upper mixed web or smaller than 60% by weight in the lower mixed web, the water-sinking property of the surface is degraded. If the amount of the pulp is larger than 60% by weight in the upper mixed web or larger than 95% by weight in the lower mixed web, the bonding strength and compression recovery ratio are degraded.

Preferably the basis weight ratio of the upper mixed web to the lower mixed web is from 0.1/1 to 1/1, especially from 0.3/1 to 1/1. If the basis weight ratio is maintained within this range, a soft touch and a good bulkiness can be imparted to the upper surface layer portion of the elastic absorbent and the flow of water from the upper surface layer portion to the lower layer is enhanced, and sinking of water in the upper surface layer portion is enhanced and a dry state can be maintained in the upper surface layer portion.

Where a liquid-permeable surface member is arranged on the upper side of the elastic absorbent having the above-mentioned sandwich structure and a liquid-impermeable surface member is arranged on the lower side, and the assembly is used as a sanitary article, preferably the surface of the intermediate layer of the polymeric water-absorbing agent is located at a position separate by 0.5 to 4 mm from the liquid-permeable surface member, as this enhances the sinking of water from the surface.

An assembly formed by arranging a liquid-permeable member such as a thin non-woven fabric or a perforated synthetic resin film on the upper side of the elastic absorbent of the present invention and a liquid-impermeable surface member such as a synthetic resin film on the lower side can be used as a sanitary article such as a sanitary napkin or a throwaway diaper. Furthermore, a tray molded from the elastic absorbent of the present invention can be used as a packaging tray for fresh fish or meat.

The present invention will now be described in detail with reference to the following examples.

In the examples, the physical properties of the obtained absorbents were determined and evaluated according to the following methods.

(1) Bonding strength (kg/25 mm)

The bonding strength of a sample having a width of 25 mm before or after absorption of water was measured at a pulling speed of 200 mm/min and a grip distance of 10 cm.

(2) Compression recovery ratio R (%)

The thickness of the sample before or after absorption of water under a predetermined load was measured, and the compression recovery ratio R in the dry or wet state was calculated according to the following formula:

$$R(1/0) = \frac{_2V_3 - _1V_{40}}{_1V_3 - _1V_{40}} \times 100$$

wherein $_1V_3$ represents the initial thickness under 3 g/cm for 1 minute, $_1V_{40}$ represents the thickness after applying a load of 40 g/cm² for 1 minute, and $_2V_3$ represents the final thickness measured after the sample was allowed to stand for 5 minutes after the measurement of $_1V_{40}$ and a load of 3 g/cm² was applied for 1 minute.

(3) Water absorption ratios AR-1 and AR-2

AR-1:

A sample having a size of 25 cm × 12 cm was immersed in artificial urine and was placed on a platinum net having a square mesh of 1 cm, and water sinking was carried out for 5 minutes and the weight was measured.

AR-2:

After measurement of AR-1, water sinking was further conducted for 5 minutes in the state inclined at 45°, and the weight was measured.

The water absorption ratio was expressed by the ratio of the weight of the sample before absorption to the weight of absorbed water.

(4) Surface water-absorbing speed (sec/ml)

Artificial urine (1 ml) was dropped on the sample surface and the time (seconds) required for artificial urine to disappear from the surface (completion of absorption) was measured.

COMPARATIVE EXAMPLE 1

A commercially available paper diaper comprising 83% of a cellulose pulp and 17% of a polymeric water-absorbing agent (a saponified acrylic acid/vinyl acetate copolymer) was used.

The properties of the elastic absorbents obtained in Examples 1 through 3 and the paper diaper of Comparative Example 1 were determined. The obtained results are shown in Table 1.

As is apparent from Table 1, the elastic absorbent of the present invention has an especially excellent bonding strength and wet compression recovery ratio.

TABLE 1

| | | Composition (%) | | | | Bonding strength (kg/25 mm) | | Compression recovery ratio (%) | | Water absorption ratio | | Surface water-absorbing speed |
|---|---|---|---|---|---|---|---|---|---|---|---|---|
| | | Pulp | Staple fibers of split yarn | Polymeric water-absorbing agent | Apparent thickness (mm) | Basis weight (g/m²) | DRY (Before absorption of water) | WET (After absorption of water) | DRY | WET | AR-1 | AR-2 | (sec/ml) |
| Example 1 | Ternary mixed web | 5 | 66 | 29 | 7.00 | 422 | 6.50 | 6.33 | 100 | 86 | 23.1 | 17.8 | Below 1.0 |
| Example 2 | Ternary mixed web | 10 | 62 | 28 | 6.70 | 419 | 4.61 | 3.69 | 88 | 67 | 20.4 | 15.0 | Below 1.0 |
| Example 3 | Ternary mixed web | 30 | 46 | 24 | 7.10 | 378 | 1.51 | 1.66 | 75 | 61 | 22.5 | 15.8 | Below 1.0 |
| Comparative Example 1 | Commercially available paper diaper | 83 | — | 17 | 6.00 | 520 | 0.07 | 0.01 | 61 | — | 21.8 | 15.7 | 1.0 |

EXAMPLE 1

According to the T-die method, crystalline polypropylene (PP) having a melting point of 163° C. and linear low-density polyethylene (LLDPE) having a density of 0.920, a melting point of 120° C. and melt flow rate of 1.2 were co-extruded so that LLDPE layers were arranged on both surfaces of the PP layer, and the extrudate was monoaxially drawn at 120° C. at a draw ratio of 5 to obtain a three-layer laminate film of LLDPE (10 μm thick)/PP (30 μm thick)/LLDPE (10 μm thick). Then, the film was slit and split according to customary procedures to obtain a split yarn having a simple fiber fineness of 10 denier. The split yarn was cut into a staple fibers having a length of 50 mm by a cutter. Simultaneously, a sheet-like cellulose pulp was pulverized and a polymeric water-absorbing agent (a saponified acrylic acid/vinyl acetate copolymer having an average particle size of 500 μm) was dispersed in the staple fibers to obtain a ternary mixed web in which the pulp/staple fibers/polymeric water-absorbing agent weight ratio was 5/66/29. The web was heat-treated at 40° C. for 5 minutes to obtain an elastic absorbent.

EXAMPLE 2

An elastic absorbent was prepared in the same manner as described in Example 1 except that staple fibers of a split yarn having a single fiber fineness of 60 denier and the pulp/staple fibers/polymeric water-absorbing agent weight ratio was changed to 10/62/28.

EXAMPLE 3

An elastic absorbent was prepared in the same manner as described in Example 1 except that staple fibers of a split yarn having a single fiber fineness of 20 denier were used and the pulp/staple fibers/polymeric water-absorbing weight ratio was changed to 30/46/24.

EXAMPLE 4

In the same manner as described in Example 1, a three-layer laminate film of LLDPE (10 μm thick)/PP (30 μm thick)/LLDPE (10 μm thick) was prepared and was then split to obtain a split yarn having an average single fiber fineness of 20 denier.

This split yarn and a sheet-like cellulose pulp were treated by an apparatus as shown in FIG. 5, and the split yarn was cut into staple fibers and mixed with the pulverized pulp by a combing roll 11 to obtain a uniform mixed web in which the staple fibers/pulp weight ratio was 60/40. The mixed web was heat-treated at 140° C. for 5 minutes. The obtained elastic absorbent had a thickness of 7 mm, a basis weight of 400 g/m² and a bonding strength (dry) of 1.5 kg/25 mm.

EXAMPLE 5

A uniform mixed web was prepared in the same manner as described in Example 4 except that a split yarn having an average single fiber fineness of 50 denier was used instead of the split yarn having an average single fiber fineness of 20 denier. The properties of an elastic absorbent obtained from this mixed web were substantially the same as those of the elastic absorbent obtained in Example 4.

COMPARATIVE EXAMPLE 2

The same split yarn as used in Example 4, which was cut in advance, and a pulverized cellulose pulp were treated by a random webber. The pulverized pulp dropped and only an uneven mixed web was obtained.

When the treatment was carried out by using a carding machine instead of the random webber, the pulverized pulp dropped and a mixed web could not be obtained.

EXAMPLE 6

Figure 7:
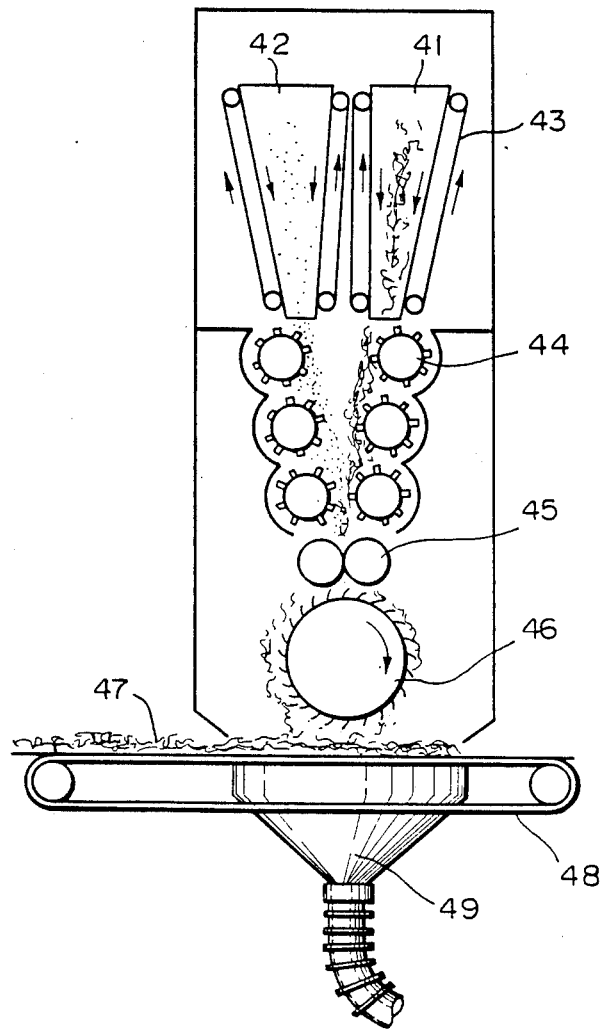

A pulverized pulp was mixed with staple fibers of a split yarn by using an apparatus as shown in FIG. 7.

Staple fibers of a split yarn having a length of 35 mm and an average single fiber fineness of 20 denier (three-layer laminate having outer layers of linear low-density polyethylene and an inner layer of crystalline polypropylene) were continuously supplied into a hopper 41 while a pulverized pulp was supplied into a hopper 42, and they were mixed at a staple fibers/pulverized pulp weight ratio of 30/70. A mixed web in which the pulverized pulp and staple fibers were uniformly dispersed was obtained on a mesh belt 48. The mixed web was heat-treated at 140° C. for 5 minutes to obtain an elastic absorbent having a thickness of 7 mm, basis weight of 400 g/m$^2$ and a bonding strength (dry) of 0.8 kg/25 mm.

EXAMPLE 7

Mixing was carried out in the same manner as described in Example 6 except that the staple fibers/pulverized pulp weight ratio was changed to 80/20. A mixed web in which the pulverized pulp and staple fibers were uniformly dispersed was obtained. The properties of an elastic absorbent prepared from this mixed web were substantially the same as those of the elastic absorbent obtained in Example 6 except that the bonding strength (dry) was 3.7 kg/25 mm.

EXAMPLE 8

A split yarn (single fiber fineness of 60 denier) was prepared from the same three-layer film of LLDPE (10 μm thick)/PP (30 μm thick)/LLDPE (10 μm thick) as obtained in Example 1. The split yarn was heated at 120° C. and powdery sodium polyacrylate having a particle size of 20 μm was fusion-bonded as the polymeric water-absorbing agent to the heated split yarn to obtain a water-absorbing split yarn having about 26% by weight of sodium polyacrylate fusion-bonding thereto.

According to the process steps shown in FIG. 6, a combing roll 11 having many needles implanted on the surface thereof was rotated at a speed of 4,000 rpm, and the water-absorbing split yarn bundle was brought into contact with the combing roll 11 to cut and shave the split yarn into staple fibers by the needles. Simultaneously, pulverized pulp was quantitatively charged into a duct 12 from a cyclone cylinder 34 and a vacuum device 17 was actuated. A mixed web in which water-absorbing staple fibers of the split yarn and the pulverized pulp were uniformly dispersed was obtained on a screen net 24.

When the mixed web was observed by a microscope, it was found that the three components were uniformly dispersed. The content of the pulverized pulp in the mixed web was 15% by weight.

The obtained mixed web was heat-treated (annealed) at 140° C. for 5 minutes in a hot air circulation dry oven. When the water absorption ratio (AR-1) was measured by using artificial urine, it was found that the water absorption ratio was 22.8.

EXAMPLE 9

In the same manner as described in Example 8, a mixed web in which 74% by weight of water-absorbing staple fibers of a split yarn having about 28.4% by weight of sodium polyacrylate fusion-bonded thereto were mixed with 26% by weight a pulverized pulp was prepared, and the mixed web was heat-treated in the same manner as described in Example 8. When the water absorption ratio (AR-1) was measured by using artificial urine, the water absorption ratio was 22.1.

COMPARATIVE EXAMPLE 3

When a preliminarily cut split yarn and a pulverized pulp were treated by a random webber, the pulverized pulp dropped and only an uneven mixed web was obtained. When sodium polyacrylate was treated together with the split yarn and pulverized pulp by the random webber, the sodium polyacrylate dropped from the mixed web and only an uneven web was obtained.

EXAMPLE 10

In the same manner as described in Example 1, a three-layer film of LLDPE (10 μm)/PP (30 μm)/LLDPE (10 μm) was prepared and split to a split yarn having an average single fiber fineness of 20 denier.

The split yarn was subjected to an action of a mixing apparatus provided with a combing roll, and simultaneously, pulverized pulp was supplied to the mixing apparatus. A uniform mixed web was obtained on an endless mesh belt. A starch/acrylic acid graft polymer (having a particle size of 150 μm) was scattered as the polymeric water-absorbing agent on the mixed web by a vibrating plate. A uniform mixed web of staple fibers of the split yarn and pulverized pulp was placed on the polymeric water-absorbing agent-scattered mixed web whereby a mixed web absorbent having a sandwich structure was continuously obtained. The obtained absorbent comprised 76% of the mixed web (30% of the pulp and 46% of the staple fibers) and 24% of the starch/acrylic acid graft polymer.

A part of the mixed web absorbent was charged in an oven and heat-treated at 140° C. for 5 minutes by blowing hot air thereto. Only the LLDPE layers were fused, and a mat-like non-woven fabric having a good elasticity and continuous air pores was obtained. When the non-woven fabric was immersed in artificial urine, the non-woven fabric absorbed the urine to cause swelling. The water absorbing property was good, and the water absorption ratio was 18.

COMPARATIVE EXAMPLE 4

Staple fibers cut from the same split yarn as used in Example 10 and pulverized cellulose pulp were treated in a random webber. The pulverized pulp dropped and only an uneven mixed web was obtained. A sandwich structure was obtained by sandwiching a starch/acrylic acid polymer (having a particle size of 150 μm) between two sheets of this mixed web.

The obtained sandwich structure was placed in an oven and heat-treated at 140° C. for 5 minutes by blowing hot air thereto to obtain a mat-like non-woven fabric. When the non-woven fabric was immersed in artificial urine, the water-absorbing speed was low and water was not absorbed in a short time.

EXAMPLE 11

According to the T-die method, crystalline polypropylene (PP) having a melting point of 163° C. and linear low-density polyethylene (LLDPE) having a density of 0.920, a melting point of 120° C. and a melt flow rate 1.2 were co-extruded so that LLDPE was arranged on both surfaces of the PP layer, and the extrudate was monoaxially drawn to obtain a three-layer laminate film of LLDPE (30 μm)/PP (90 μm)/LLDPE (30 μm) having a total thickness of 150 μm or a three-layer laminate film of LLDPE (10 μm)/PP (30 μm)/LLDPE (10 μm) having a total thickness of 50 μm. Then, each film was slit and split according to customary procedures to obtain a split yarn having a single fiber fineness of 60 to 20 denier. By using an apparatus as shown in FIG. 6, the split yarn was treated by a combing roll to form staple fibers, and simultaneously, the staple yarns were dry-blended with a pulverized cellulose pulp. Thus, two mixed webs were obtained.

In the mixed web containing staple fibers of the split yarn having the single fiber fineness of 60 denier, the pulp/staple fibers weight ratio was adjusted 13.8/86.2, and in the mixed web containing the staple fibers of the split yarn having a single fiber fineness of 20 denier, the pulp/staple fibers weight ratio was adjusted to 73.2/26.8. A sandwich structure was formed by using the former mixed web as the upper layer and the latter mixed web as the lower layer and interposing powdery potassium polyacrylate (having an average particle size of 200 μm) as the polymeric water-absorbing agent between the two mixed webs. In this sandwich structure, the total pulp/staple fibers weight ratio was 58.4/41.6, and the basis weight ratio of the former mixed web to the latter mixed web was 0.33/1. In this sandwich structure, the pulp/staple fibers/polymeric water-absorbing agent weight ratio was 45.1/32.2/22.7.

The sandwich structure was heat-treated at 140° C. for 5 minutes in an air oven to obtain a softness and a good flexibility. The water-sinking property of the upper layer portion was very good and the upper layer portion was dry, and the absorbent had a good elasticity as a whole.

EXAMPLE 12

An elastic absorbent was prepared in the same manner as described in Example 11 except that the pulp/staple fibers weight ratio in the upper layer was changed to 13.8/86.2, the pulp/staple fibers weight ratio in the lower layer was changed to 60.3/39.7, the total pulp/staple fibers weight ratio was changed to 47.9/52.1, and the pulp/staple fibers/polymeric water-absorbing agent weight ratio in the entire elastic absorbent was changed to 37.6/39.7/22.7. The elastic absorbent was soft and had a good flexibility, and the upper layer portion had a good water-sinking property and was dry. The absorbent had a good elasticity as a whole.

EXAMPLE 13

An elastic absorbent was prepared in the same manner as described in Example 11 except that the pulp/staple fibers weight ratio in the upper layer was changed to 13.9/86.1, the pulp/staple fibers weight ratio in the lower layer was changed to 73.1/26.9, the total pulp/staple fibers weight ratio was changed to 43.5/56.5, the pulp/staple fibers/polymeric water-absorbing agent weight ratio in the entire absorbent was changed to 33.5/43.5/23 and the basis weight ratio of the upper layer to the lower layer was changed to 1/1. The elastic absorbent was soft and had a good flexibility, and the surface layer had a good water-sinking property and was dry. The absorbent had a good elasticity as a whole.

The properties of the absorbents obtained in Examples 11 through 13 are shown in Table 2.

TABLE 2

| | Pulp/staple fibers weight ratio | | | Pulp/staple fibers/polymeric water-absorbing agent weight ratio in entire absorbent | Upper layer/lower layer basis weight ratio | Apparent thickness (mm) | Bonding strength (kg/25 mm) | | Compression recovery ratio (%) | | Water absorption ratio | | Surface water-absorbing speed (sec/ml) |
|---|---|---|---|---|---|---|---|---|---|---|---|---|---|
| | Pulp (upper layer/lower layer) | Staple fibers (upper layer/lower layer) | Total pulp/staple fibers weight ratio | | | | DRY | WET | DRY | WET | AR-1 | AR-2 | |
| Example 11 | 13.8/73.2 | 86.2/26.8 | 58.4/41.6 | 45.1/32.2/22.7 | 0.33/1 | 7.6 | 0.7 | 0.6 | 80 | 62 | 24.1 | 17.0 | 0.2> |
| Example 12 | 13.8/60.3 | 86.2/39.7 | 47.9/52.1 | 37.6/39.7/22.7 | 0.33/1 | 8.0 | 1.1 | 1.0 | 82 | 66 | 23.4 | 17.7 | 0.2> |
| Example 13 | 13.9/73.1 | 86.1/26.9 | 43.5/56.5 | 33.5/43.5/23 | 1/1 | 10.3 | 1.8 | 1.4 | 73 | 59 | 24.7 | 16.3 | 0.2> |

EXAMPLE 14

In the same manner as described in Example 1, staple fibers of a split yarn were prepared from LLDPE having a melting point of 120° C. and a melt flow rate of 0.8 and crystalline PP having a melting point of 163° C. and a melt flow rate of 1.5 and the staple fibers were mixed with pulverized pulp to obtain a mixed web. Sodium polyacrylate having a particle size of 170 μm was placed on the mixed web to form a thin layer of sodium polyacrylate. Then, another mixed web prepared in the same manner as described above was placed in a thickness of 2 mm on this thin layer, whereby an absorbing layer was formed.

The obtained absorbing layer as a whole comprised 30% of the pulverized pulp, 46% of the staple fibers of the split yarn and 24% of sodium polyacrylate. A polypropylene non-woven fabric having a thickness of 80 μm was placed on the absorbing layer to obtain an absorbent in which the surface of the thin layer of sodium polyacrylate was located apart by 2 mm from the surface of the non-woven fabric.

When urine was dropped on the surface of the absorbent, urine sank from the surface in a short time, and the surface was dry and had a good touch to the skin.

COMPARATIVE EXAMPLE 5

An absorbent in which the surface of a thin layer of sodium polyacrylate was located apart by 0.3 mm from the surface of a non-woven fabric was prepared in the same manner as described in Example 14 except that the pulverized pulp and tissue paper were placed in a thickness of 0.3 mm on the thin layer of sodium polyacrylate to form an absorbing layer (pulp/polymeric water-absorbing agent weight ratio=70/30).

When urine was dropped on the surface of the absorbent, water sinking was possible but a long time was necessary, and the surface was always wet and the touch to the skin was not good.

EXAMPLE 15

A three-layer inflation film having a thickness of 50 μm was prepared by using compositions described below under conditions described below, and the film was slit, drawn by a hot roll, split by a splitting roll, and webbed and mixed with pulverized pulp according to procedures described below.

| Outermost layer | |
|---|---|
| Screw diameter: | 40 mm |
| Cylinder temperature $C_1$: | 170° C. |
| $C_2$: | 230° C. |
| H.D: | 220° C. |

High-density polyethylene having a melting point of 135° C., a melt flow rate of 1.0 and containing 2% of a pigment, was molten and extruded.

| Intermediate layer | |
|---|---|
| Screw diameter: | 40 mm |
| Cylinder temperature $C_1$: | 180° C. |
| $C_2$: | 220° C. |
| $C_3$: | 230° C. |
| H: | 230° C. |
| $D_1$, $D_2$: | 230° C. |

Crystalline polypropylene having a melting point of 163° C. and a melt flow rate of 1.5 and containing 2% of a pigment was molten and extruded.

Innermost layer
Screw diameter: 32 mm
Other conditions were the same as those for the outermost layer.

The die lip clearance was adjusted to 1 mm and the film was taken up at a take-up speed of 10.7 m/min. The film was slit to adjust the tape width to 8 mm. The film was drawn at a drawing roll temperature of 120° C. and a draw ratio of 5 and was then split by a splitting roll. More specifically, the film having a fineness of 1,500 denier was split to a split yarn having a single fiber fineness of 10 denier by the splitting roll.

The split yarn was cut into staple fibers by a combing roll having many needles implanted on the surface thereof, and simultaneously, the staple fibers were mixed with pulverized pulp to obtain a mixed web (pulp/staple fibers weight ratio=65/35). The mixed web was placed in an over of the hot air circulation type and was heat-treated at 150° C. for 5 minutes to obtain an absorbent. The absorbent was contained in a casing comprising a high-density polyethylene film (leakage-preventing sheet) (25 μm in thickness) and a non-woven fabric to form a sanitary napkin.

The absorbent of this napkin was only slightly contracted by absorption of a liquid. The napkin was soft and had an excellent comfort.

EXAMPLE 16

A foamed water-cooled three-layer inflation film having a thickness of 50 μm was prepared by using compositions described below under conditions described below.

| Outermost layer | |
|---|---|
| Screw diameter: | 40 mm |
| Cylinder temperature $C_1$: | 170° C. |
| $C_2$: | 190° C. |
| H.D: | 200° C. |

Linear low-density polyethylene having a melt flow rate of 2.0 and containing 0.2% of azodicarbonamide (Celumike CE supplied by Sankyo Kasei) was molten and extruded.

| Intermediate layer | |
|---|---|
| Screw diameter: | 65 mm |
| Cylinder temperature $C_1$: | 170° C. |
| $C_2$: | 180° C. |
| $C_3$: | 190° C. |
| $C_4$: | 200° C. |
| H: | 200° C. |
| $D_1$, $D_2$: | 200° C. |

Crystalline polypropylene having a melt flow rate of 3.5, which contained 0.3% of the above-mentioned azodicarbonamide, was molten and extruded.

Innermost layer
Screw diameter: 40 mm
Other conditions were the same as those for the outermost layer.

The die lip clearance was adjusted to 1.4 mm, and the film was taken up at a take-up speed of 35 m/min. The film was slit to adjust the tape width to 8 mm and the film was drawn at a drawing roll temperature of 103° C. and a draw ratio of 5. Then, the drawn film was split by a splitting roll. More specifically, the film having a fineness of 1,000 denier was split to an average single fiber fineness of 6 denier by the splitting roll.

The obtained split yarn was converted to staple fibers by a combing roll having many needles implanted on the surface thereof and simultaneously, the staple fibers were mixed with pulverized pulp to obtain a mixed web (pulp/staple fibers weight ratio=65/35). A sanitary napkin was prepared from this mixed web in the same manner as described in Example 15. This sanitary napkin was further improved in the touch over the napkin obtained in Example 15.

We claim:
1. An apparatus for the preparation of an elastic absorbent composed of a mixed web, said apparatus comprises
    two supply hoppers for separately supplying pulverized pulp and staple fibers of a synthetic fiber split yarn at a constant mixing ratio, each hopper having a pair of confronting moving belts for said supplying,
    two guide mechanisms each comprising at least two gear guides disposed below said hoppers for guiding and mixing the supply of the pulverized pulp and staple fibers, said gear guides in each of the guide mechanisms being arranged in series so that the two guide mechanisms confront each other and the distance between the confronting two guide mechanisms downwardly becomes narrower,
    a pair of nip rollers disposed below the guide mechanisms to compress the pulverized pulp and staple fibers.
    a garnet roll disposed below the pair of the nip rollers to disintegrate and mix the pulverized pulp and staple fibers, and
    a vacuum device disposed below the garnet roll with a mesh belt being interposed therebetween to pull the pulverized pulp and staple fiber mixture onto the mesh belt.

* * * * *